US012752103B2

(12) United States Patent
Doerr et al.

(10) Patent No.: US 12,752,103 B2
(45) Date of Patent: Oct. 6, 2026

(54) LEAD FOR AN IMPLANTABLE STIMULATION DEVICE FOR CARDIAC STIMULATION OF A PATIENT

(71) Applicant: BIOTRONIK SE & Co. KG, Berlin (DE)

(72) Inventors: Thomas Doerr, Berlin (DE); Gernot Kolberg, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 365 days.

(21) Appl. No.: 17/772,285

(22) PCT Filed: Oct. 23, 2020

(86) PCT No.: PCT/EP2020/079847
§ 371 (c)(1),
(2) Date: Apr. 27, 2022

(87) PCT Pub. No.: WO2021/083794
PCT Pub. Date: May 6, 2021

(65) Prior Publication Data

US 2022/0370789 A1 Nov. 24, 2022

(30) Foreign Application Priority Data

Nov. 1, 2019 (EP) .................................... 19206697

(51) Int. Cl.
*A61N 1/05* (2006.01)
*A61N 1/368* (2006.01)

(52) U.S. Cl.
CPC ............... *A61N 1/05* (2013.01); *A61N 1/368* (2013.01)

(58) Field of Classification Search
CPC ........ A61N 1/05; A61N 1/368; A61N 1/0563; A61N 1/568; A61N 1/0573; A61N 1/3627;
(Continued)

(56) References Cited

U.S. PATENT DOCUMENTS 5,728,140 A * 3/1998 Salo ....................... A61N 1/056
607/9
6,741,893 B2 5/2004 Smits
(Continued)

FOREIGN PATENT DOCUMENTS

EP 0919254 A2 6/1999
WO 2014036317 A2 3/2014
WO 2019079456 A1 4/2019

OTHER PUBLICATIONS

International Search Report (PCT/ISA/210) and Written Opinion (PCT/ISA/237) mailed on Jan. 13, 2021, by the European Patent Office as the International Searching Authority for International Application No. PCT/EP2020/079847.

*Primary Examiner* — Niketa Patel
*Assistant Examiner* — Sebastian X Lukjan
(74) *Attorney, Agent, or Firm* — Buchanan Ingersoll & Rooney PC

(57) ABSTRACT

A lead for an implantable stimulation device for cardiac stimulation of a patient generally extends along a longitudinal axis. The lead comprises a body section, a distal lead section extending from the body section along the longitudinal axis and forming a distal end, a first electrode device arranged on the distal lead section for at least one of transmitting an electrical pacing signal and sensing an electrical sense signal, the first electrode device being configured for placement in or on intra-cardiac tissue, and a second electrode device arranged on the body section for emitting an electrical defibrillation signal. The distal lead
(Continued)

section in at least one portion comprises a reduced bending stiffness with respect to at least a portion of said body section.

8 Claims, 4 Drawing Sheets

(58) Field of Classification Search
CPC ...... A61N 1/056; A61N 1/0565; A61N 1/057; A61N 1/3684
See application file for complete search history.

(56) References Cited

U.S. PATENT DOCUMENTS

| | | | | |
|---|---|---|---|---|
| 7,127,302 | B2 * | 10/2006 | Palm | A61N 1/0565 600/375 |
| 2004/0064158 | A1 * | 4/2004 | Klein | A61N 1/056 607/9 |
| 2013/0231728 | A1 | 9/2013 | Ollivier | |
| 2014/0046389 | A1 * | 2/2014 | Anderson | A61N 1/3684 607/4 |
| 2019/0111265 | A1 | 4/2019 | Zhou | |
| 2021/0023367 | A1 * | 1/2021 | Ghosh | A61N 1/0573 |

* cited by examiner

LEAD FOR AN IMPLANTABLE STIMULATION DEVICE FOR CARDIAC STIMULATION OF A PATIENT

CROSS-REFERENCE TO RELATED APPLICATIONS

This application is the United States National Phase under 35 U.S.C. § 371 of PCT International Patent Application No. PCT/EP2020/079847, filed on Oct. 23, 2020, which claims the benefit of European Patent Application No. 19206697.5, filed on Nov. 1, 2019, the disclosures of which are hereby incorporated by reference herein in their entireties.

TECHNICAL FIELD

The present invention relates a lead for an implantable stimulation device for cardiac stimulation of a patient according to the preamble of claim 1.

BACKGROUND

A lead of this kind generally extends along a longitudinal axis and comprises a body section, a distal lead section extending from the body section along the longitudinal axis and forming a distal end, a first electrode device arranged on the distal lead section and a second electrode device arranged on the body section. The first electrode device herein serves to at least one of transmit an electrical pacing signal and sense an electrical sense signal, the first electrode device being configured for placement in or on intra-cardiac tissue, such that the first electrode device electrically contacts with intra-cardiac tissue. The second electrode device, in turn, serves to emit an electrical defibrillation signal.

A lead of this kind may, for example, be used on an implantable stimulation device, e.g., in the shape of a CRT device which may be subcutaneously implanted in a patient, for example in the region of the collarbone of a patient. One or multiple leads herein extend from the stimulation device, the leads extending into the patient's heart for providing for an intra-cardiac stimulation action, in particular a pacing action and a defibrillation action. Because a (single) lead comprises different electrode devices, a pacing and/or sensing action as well as a defibrillation may be achieved by means of a single lead.

The lead may, for example, extend, in an implanted state, into the right ventricle of the patient's heart. There herein is a general desire to combine an effective physiological stimulation with a defibrillation therapy. For an effective physiological stimulation, herein, approaches exist to provide for a stimulation at the so-called left bundle branch, in particular to provide a (re-)synchronization therapy in case of a so-called left bundle block. As for a stimulation at the left bundle branch a lead cannot be fixed at the vertex of the right ventricle, but is to be implanted to extend towards the septum of the heart to engage with the left bundle branch, a lead for providing for a left bundle branch stimulation may not be easily combined with a defibrillation (ICD) therapy.

International Publication No. WO 2019/079456 A1 discloses an arrangement for providing for an HIS bundle or bundle branch pacing in a cardiac pacing system to achieve synchronized ventricular activation. Bundle pacing may be delivered in response to determining whether a QRS parameter or activation interval is greater than a threshold. A set of AV delays may be generated, and an optimal AV delay may be selected from the stored set of AV delays.

The present disclosure is directed toward overcoming one or more of the above-mentioned problems, though not necessarily limited to embodiments that do.

SUMMARY

It is an object of the instant invention to provide a lead for an implantable stimulation device for cardiac stimulation of a patient which allows for a left bundle branch stimulation for providing for a pacing action in a patient's heart in combination with a defibrillation therapy.

At least this object is achieved by means of a lead comprising the features of claim 1.

Accordingly, the distal lead section of the lead in at least one portion comprises a reduced bending stiffness with respect to at least a portion of the body section of the lead.

For achieving a left bundle branch pacing, the first electrode device of the lead, which is arranged on the distal lead section of the lead, is to be placed on intra-cardiac tissue in the vicinity of the left bundle branch, that is on the septum of the patient's heart. Hence, the distal lead section, in an implanted state, comes to rest on the septum of the heart at a substantial distance from the vertex of the right ventricle (in case of implantation of the lead in the right ventricle), in the region of which, however, the second electrode device should be placed in order to enable an effective defibrillation action in the right ventricle.

Hence, in order to allow a combination of a first electrode device (configured for providing for a pacing action in the region of the left bundle branch or for sensing signals in the region of the left bundle branch) and a second electrode device (configured for providing for a defibrillation action) on a single lead the distal lead section is formed to be flexibly bendable such that the lead, with its distal lead section, may be placed on the septum of the heart in the region of the left bundle branch and may extend from a location of fixation to bend towards the vertex of the right ventricle in order to allow a placement of the second electrode device in the region of the vertex of the right ventricle. The lead hence may assume a curved, bent shape within the right ventricle, allowing the second electrode device to be received within the right ventricle in the vicinity of the vertex of the right ventricle.

A first electrode device configured for transmitting an electrical pacing signal and/or for sensing an electrical sense signal, in particular in the region of the left bundle branch of the conduction system of the patient's heart, hence may be combined with a second electrode device configured for emitting an electrical defibrillation signal. Using a single lead, hence, a left bundle branch pacing therapy may be combined with a defibrillation therapy. Because the lead may be implanted into the patient's heart such that the distal lead section with the first electrode device arranged thereon comes to rest in the region of the left bundle branch and may electrically contact the left bundle branch, a pacing at the left bundle branch may be provided, allowing for a physiological stimulation by achieving a propagation of stimulation signals along the bundle branches of the ventricles at low stimulation thresholds. A left bundle branch stimulation may allow for an easy and reliable implantation and easy stimulation algorithms, in particular not requiring a particular adjustment of AV delays as necessary, for example, for an HIS bundle pacing.

In one embodiment, the distal lead section in at least one portion comprises a reduced bending stiffness with respect to a portion of the body section carrying the second electrode device. The distal lead section, hence, is flexibly bendable, in particular with respect to the portion of the body section which carries the second electrode device. Because the distal lead section is flexibly bendable, it may assume a shape such that the second electrode device may be placed in the region of the vertex of the right ventricle, the distal lead section extending from the body section towards a fixation site on the septum of the heart for achieving a left bundle branch pacing.

In one embodiment, the distal lead section comprises an iso-diametric cross-sectional shape. In addition or alternatively, the body section comprises an iso-diametric cross-sectional shape. The distal lead section herein may comprise a first diameter, whereas the body section comprises a second diameter larger than the first diameter. Because the distal lead section may have a reduced diameter with respect to the body section, the bending stiffness of the distal lead section may be reduced, such that the distal lead section may be flexibly bent to allow a placement of the second electrode device in the region of the vertex of the right ventricle.

The bending stiffness generally describes the resistance of a respective member against bending deformation. It is in particular a function of the Young's modulus E, and the area moment of inertia I of the cross-section of the respective section about the axis of interest.

In one embodiment, the distal lead section comprises a length, measured between the distal end and the body section, equal to or larger than 10 mm, preferably equal to or larger than 20 mm, even more preferably equal to or larger than 30 mm, even more preferably equal to or larger than 40 mm, even more preferably equal to or larger than 50 mm. Because the distal lead section extends over a substantial length from the body section and the second electrode device arranged thereon, the distal lead section may easily bend with respect to the body section and allows for a placement of the second electrode device arranged on the body portion at a substantial distance from a fixation site at which the distal end formed by the distal lead section is fixed on intra-cardiac tissue, in particular on the septum in the region of the left bundle branch for achieving a left bundle branch pacing. Because the distal lead section comprises a substantial length, the lead may form a curved loop within the right ventricle, the loop reaching into the region of the vertex of the right ventricle, such that the second electrode device may come to rest in the region of the vertex of the right ventricle, hence allowing for a defibrillation in the region of the vertex of the right ventricle.

In one embodiment, the first electrode device is arranged at the distal end formed by the distal lead section. By placing the distal end on intra-cardiac tissue, hence, the first electrode device may be brought into contact with intra-cardiac tissue, in particular in the region of the left bundle branch in order to allow for a pacing or a sensing of signals at the left bundle branch.

In one embodiment, the first electrode device is configured to pierce into intra-cardiac tissue for fixing the lead at the distal end to intra-cardiac tissue. The first electrode device hence serves to electrically contact with intra-cardiac tissue in order to provide for an electrical pacing and/or sensing, and at the same time serves to provide for a mechanical fixing of the lead on intra-cardiac tissue. For this, the first electrode device, for example, may have the shape of a screw, which may be screwed into intra-cardiac tissue in order to engage with intra-cardiac tissue to fix the lead to intra-cardiac tissue.

The first electrode device may be formed from an electrical conductor, for example by forming the screw from an electrically conductive material which, along its entire length, may contact with intra-cardiac tissue. Alternatively, the electrode device may comprise one or multiple contact sections, formed, for example, from sections of the screw which are exposed towards the outside and may contact with intra-cardiac tissue. In other regions an insulating layer may provide for an electrical insulation, such that the electrode device, for example formed as a screw, may electrically contact with intra-cardiac tissue only in the region of the one or the multiple contact sections.

By means of the first electrode device, beneficially an emission of pacing signals or a reception of sensing signals in the region of the left bundle branch of the electrical conduction system of the heart shall be enabled. For this, the first electrode device, in one embodiment, extends from the distal end by a length, as measured along the longitudinal axis, such that the first electrode device may be placed on and engaged with intra-cardiac tissue to reach into the left bundle branch within the septum of the heart, in particular when implanting the lead in the right ventricle of the heart. The first electrode device hence allows for a deep engagement in particular in the septum of the heart, such that the first electrode device may electrically contact with the left bundle branch and hence may inject pacing signals into and receive sense signals from left bundle branch.

The first electrode device, for example in the shape of a screw, herein may have a diameter, measured in a transverse direction transverse to the longitudinal axis, which is equal to or only slightly smaller than the diameter of the distal lead section. In this way, by inserting the first electrode device into intra-cardiac tissue (for example by screwing the first electrode device in the shape of a screw into intra-cardiac tissue), the electrode device may be engaged with intra-cardiac tissue, wherein also a portion of the distal lead section may be inserted into intra-cardiac tissue when, e.g., screwing the electrode device into intra-cardiac tissue.

In one embodiment, the distal lead section comprises a drug reservoir, such as a steroid eluting reservoir. The reservoir may be configured to elute, in an implanted state of the lead, the drug towards intra-cardiac tissue in order to, for example, reduce or prevent a rise of a stimulation threshold after implantation.

In one embodiment, the second electrode device comprises a helical coil shape. The second electrode device may, for example, be formed from a coil wound about the body section of the lead or embedded into the body section, the second electrode device having a surface area sufficiently large to allow for an emission of defibrillation signals for providing for a defibrillation therapy.

In one embodiment, the second electrode device is formed from a single electrode, having, for example, a helical coil shape. The second electrode device may be received in particular in the region of the vertex of the right ventricle, such that defibrillation signals may be emitted from the second electrode device in the course of a defibrillation therapy.

In one embodiment, the second electrode device comprises a first electrode section and a second electrode section formed, for example, from separate helical coils. The lead herein comprises a connection section extending in between the first electrode section and the second electrode section, such that the first electrode section and the second electrode section are spatially separated from one another.

Herein, in one embodiment, the connection section in at least one portion comprises a reduced bending stiffness with respect to a portion of the body section carrying the first electrode section and/or to a portion of the body section carrying the second electrode section. The connection section, hence, may be flexibly bendable, allowing to arrange portions of the body section carrying the electrode sections of the second electrode device at a (sharp) angle with respect to one another. This may facilitate fitting the lead into the vertex of the right ventricle. By providing different electrode sections of the second electrode device, in addition, an active electrode length may be increased, allowing, for example, to reduce a diameter of the lead, because an increase of the active length may allow for a reduction of the cross-sectional shape of the second electrode device.

The connection section in particular may allow for a tight bending radius. Hence, the different electrode sections of the second electrode device may be arranged at a rather sharp angle with respect to one another, allowing to place the lead with the electrode sections arranged thereon in the region of the vertex of the right ventricle.

In another aspect, a method for operating an implantable stimulation device for cardiac stimulation of a patient comprises: providing a lead generally extending along a longitudinal axis, the lead comprising a body section and a distal lead section extending from the body section along the longitudinal axis and forming a distal end, the lead further comprising a first electrode device arranged on the distal lead section for at least one of transmitting an electrical pacing signal and sensing an electrical sense signal and a second electrode device arranged on the body section for emitting an electrical defibrillation signal. The method further comprises: using the first electrode device, which is placed on intra-cardiac tissue to reach into a left bundle branch of the cardiac conduction system, to at least one of inject pacing signals into or receive sense signals from the left bundle branch.

All aspects as described above are combinable with the method, such that the advantages and advantageous embodiments described above for the lead equally apply also to the method.

A lead as described herein may be connected to a stimulation device. One or multiple leads herein may be connected to the stimulation device, which, for example, may be subcutaneously implanted in a patient. The connection of the lead to the stimulation device herein may be achieved, for example, by a connector, for example a DF4 connector formed on the lead.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

An idea of the present invention shall subsequently be described in more detail with reference to the embodiments shown in the figures. Herein.

DETAILED DESCRIPTION

Figure 1:
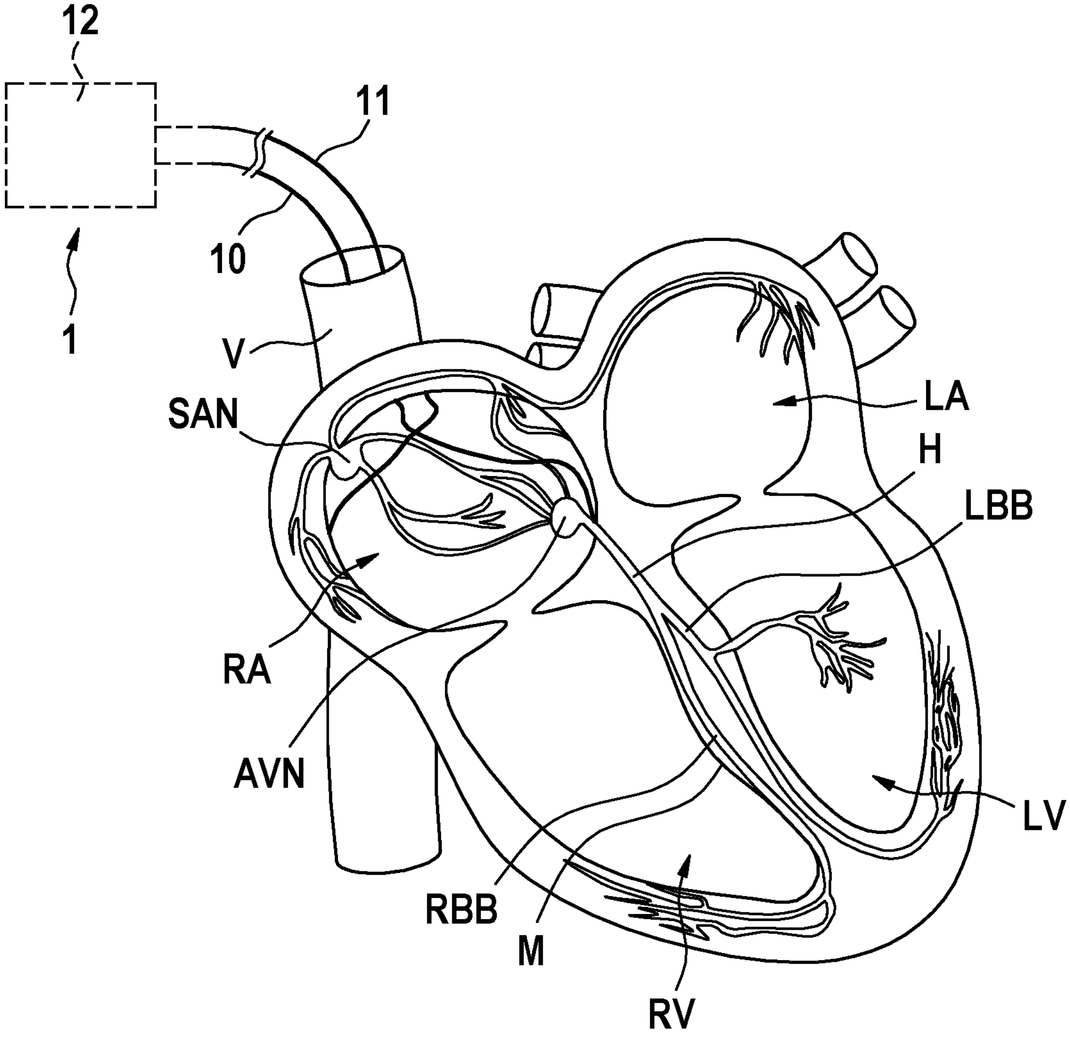
FIG. 1 shows a schematic view of the human heart, including the Sinoatrial node, the Atrioventricular node, the HIS bundle and the left bundle branch and right bundle branch extending from the HIS bundle.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

FIG. 1 shows, in a schematic drawing, the human heart comprising the right atrium RA, the right ventricle RV, the left atrium LA and the left ventricle LV, the so-called sinoatrial node SAN being located in the wall of the right atrium RA, the sinoatrial node SAN being formed by a group of cells having the ability to spontaneously produce an electrical impulse that travels through the heart's electrical conduction system, thus causing the heart to contract in order to pump blood through the heart. The atrioventricular node AVN serves to coordinate electrical conduction in between the atria and the ventricles and is located at the lower back section of the intra-atrial septum near the opening of the coronary sinus. From the atrioventricular node AVN the so-called HIS bundle H is extending, the HIS bundle H being comprised of heart muscle cells specialized for electrical conduction and forming part of the electrical conduction system for transmitting electrical impulses from the atrioventricular node AVN via the so-called right bundle branch RBB around the right ventricle RV and via the left bundle branch LBB around the left ventricle LV.

In the embodiment of FIG. 1, an implantable medical device 1 in the shape of a stimulation device, such as a CRT device, is implanted in a patient, the implantable medical device 1 comprising a generator 12 connected to leads 10, 11 extending from the generator 12 through the superior vena V into the patient's heart. By means of the leads 10, 11, electrical signals for providing a pacing action in the heart shall be injected into intra-cardiac tissue potentially at different locations within the heart, and sense signals may be received. In addition, a defibrillation therapy may be performed by an electrode arrangement arranged on one or both of the leads 10, 11.

Figure 2:
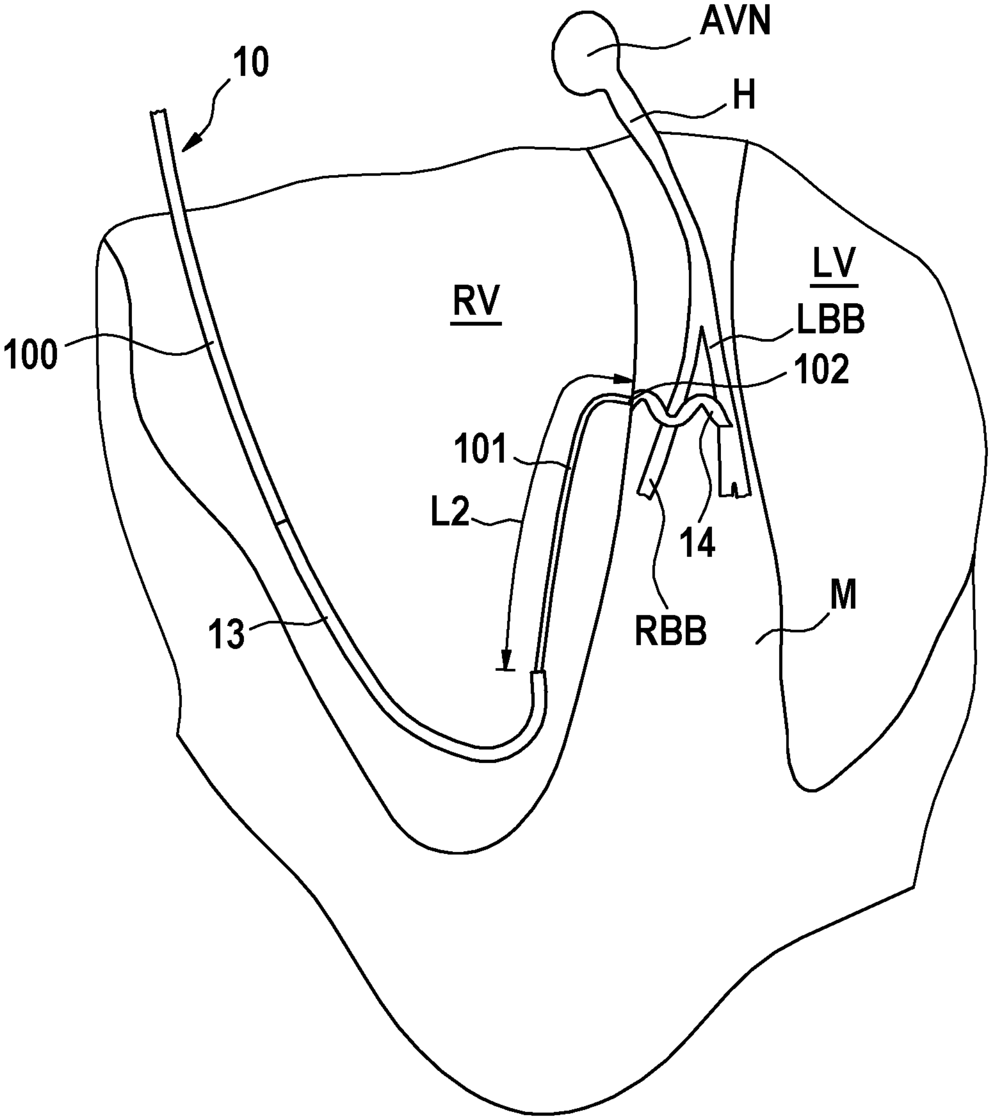
FIG. 2 shows a view of an embodiment of a lead placed in the right ventricle of the heart for providing for a left bundle branch pacing as well as a defibrillation therapy.

In an embodiment shown in FIG. 2, a lead 10 is implanted into the heart such that it extends into the right ventricle RV of the heart and, at a distal end 102, is arranged on intra-cardiac tissue at the septum M in between the right ventricle RV and the left ventricle LV of the heart. At the distal end 102 herein an electrode device 14 in the shape of a screw is arranged, the electrode device 14 being screwed into intra-cardiac tissue for injecting electrical signals into the intra-cardiac tissue or for receiving sense signals from the intra-cardiac tissue.

Figure 3:
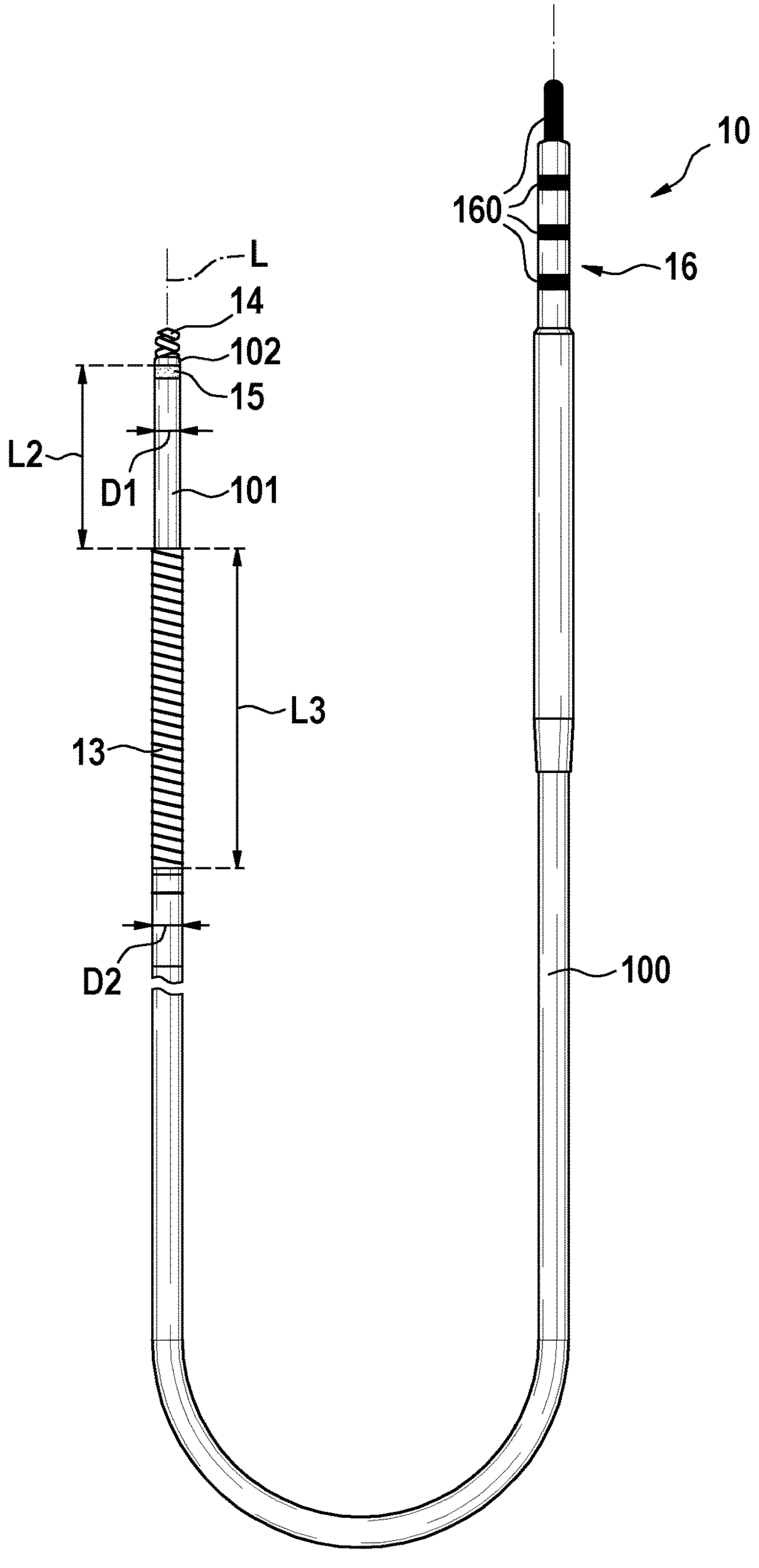
FIG. 3 shows an embodiment of a lead combining electrodes for a left bundle branch pacing and a defibrillation therapy.

An embodiment of such a lead 10 is shown in FIG. 3. The lead 10 comprises a body section 100 having a tube shape and forming, for example, an inner lumen. The body section 100 carries an electrode device 13 which comprises a coil shape and is wound about or embedded in the body section 100, the electrode device 13 serving as a shock electrode for providing for a defibrillation function in an implanted state of the lead 10. A distal lead section 101 extends from the body section 100 distally from the electrode device 13, the distal lead section 1 carrying, at a distal end 102, the electrode device 14 in the shape of the screw to be engaged with intra-cardiac tissue for fixing the lead 10 into intra-cardiac tissue at the distal end 102.

Figure 4:
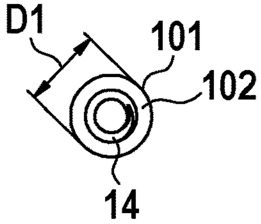
FIG. 4 shows a front view of a distal end of the lead.

In one embodiment, both the body section 100 and the distal lead section 101 comprise an iso-diametric cross-section, as this is visible, e.g., from FIG. 4. Herein, the distal lead section 101 comprises a reduced bending stiffness in that the diameter D1 of the distal lead section 101 is reduced in comparison to the diameter D2 of the body section 100. Hence, the distal lead section 101 with the electrode device 14 arranged thereon may be flexibly bent, a stiffness along the length L2 of the distal lead section 101 being reduced with respect to the body section 100, in particular the portion of the body section 100 carrying the electrode device 13.

This allows, as this is shown in FIG. 2, to arrange the lead 10 in the right ventricle RV such that the electrode device 14 on the distal end 102 formed by the distal lead section 101 comes to rest on the septum M in the range of the right bundle range RBB and the left bundle range LBB. Herein, the electrode device 14 in the shape of the screw, in addition to its electrical function, provides a fixation means which may be screwed into the septum M such that the electrode device 14 provides for a fixation within the septum M. By means of the electrode device 14 the lead 10 at its distal end 102 hence is fixed to the septum M and held in place on the septum M.

As visible from FIG. 2, the electrode device 14 may be inserted into the septum M such that it reaches, from the right ventricle RV, towards the left bundle branch LBB and engages with the left bundle branch LBB for injecting stimulation signals into the left bundle branch LBB for providing for a pacing using the left bundle branch LBB. In addition or alternatively, sense signals may be received from the left bundle branch LBB.

Figure 6:
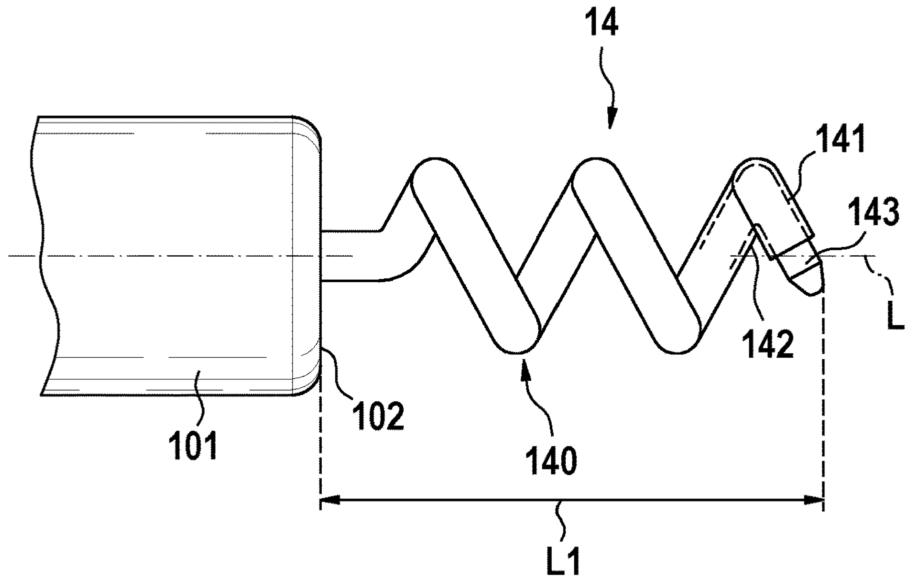
FIG. 6 shows an embodiment of an electrode device arranged on a distal end of a distal lead section.

Referring now to FIG. 6, the electrode device 14, in one embodiment, comprises the shape of a screw extending over a length L1 from the distal end 102, as measured along a longitudinal axis L along which the lead 10 generally extends. The length L1 herein is chosen such that the electrode device 14 may be inserted into the septum M such that it reaches into a depth at which the left bundle branch LBB is placed, such that a left bundle branch pacing or sensing may be achieved by means of the lead 10.

As visible from FIG. 6, the electrode device 14 in one embodiment may comprise a body 140 formed by an electrically conductive core 141 which extends along the electrode device 14 and in portions is covered by an insulating layer 142. For example, the core 141 is exposed towards the outside only at a distal end 143 forming a contact section for electrically contacting intra-cardiac tissue. In this way it can be achieved that the electrode device 14 extends across the right bundle branch RBB, as visible from FIG. 2, towards the left bundle branch LBB, but electrically contacts only the left bundle branch LBB for providing a pacing and/or sensing at the left bundle branch LBB.

In an alternative embodiment, the electrode device 14 may be electrically conducting and exposed along its entire length L1 and may contact electrically with intra-cardiac tissue along its entire length L1. In such embodiment, for example, a synchronous pacing at the right bundle branch RBB and the left bundle branch LBB by means of the electrode device 14 may be achieved.

Referring now again to FIG. 3, a reservoir 15 may be formed in the region of the distal end 102 of the distal lead section 101, the distal lead section 101, for example, comprising a drug reservoir such as a steroid eluting reservoir to be emitted towards intra-cardiac tissue for reducing or preventing a rise of a stimulation threshold after implantation.

As visible from FIG. 3 and FIG. 4, the electrode device 14 in the shape of a screw has a diameter which is only slightly smaller than the diameter of the distal lead section 101. This may allow to screw the electrode device 14 into the septum M such that also at least a portion of the distal end section 101 is introduced into the septum M, bringing the reservoir 15, for example, into contact with intra-cardiac tissue.

Referring now again to FIG. 2, because the distal lead section 101 comprises an increased bending flexibility with respect to the body section 100 of the lead 10, the lead 10 may be arranged in the right ventricle RV such that a loop is formed, the electrode device 13 serving as a shock electrode being placed in the region of the vertex of the right ventricle RV. Because the distal lead section 101 is substantially flexible, the distal end 102 formed by the distal lead section 101 may be placed on the septum M in the region of the left bundle branch LBB, the distal lead section 101 assuming a rather tight bending radius allowing the electrode device 13 to come to rest in the region of the vertex of the right ventricle RV and hence allowing for an efficient defibrillation action.

To allow the distal lead section 101 to flexibly bend such that the electrode device 13 may reach into and come to rest in the region of the vertex of the right ventricle RV, the length L2 of the distal lead section 101 may be equal to or larger than 10 mm, preferably equal to or larger than 20 mm, more preferably equal to or larger than 30 mm, even more preferably equal to or larger than 40 mm or even 50 mm. The distal lead section 101 hence comprises a length L2 allowing the electrode device 13 to be arranged at a substantial distance from the left bundle branch LBB to which the distal end 102 of the distal lead section 101 with the electrode device 14 arranged thereon is connected.

Referring now again to FIG. 3, the lead 10, at a proximal end, comprises a connector 16 having contacts 160 for electrically contacting with a connector block of the generator 12. The connector 16 may, for example, have the shape of a (standardized) DF4 connector.

In the embodiment of FIGS. 2 and 3, the electrode device 13 serving as a shock electrode for a defibrillation therapy extends over a length L3 on the body section 100, the electrode device 13 being formed by a continuously wound coil.

Figure 5:
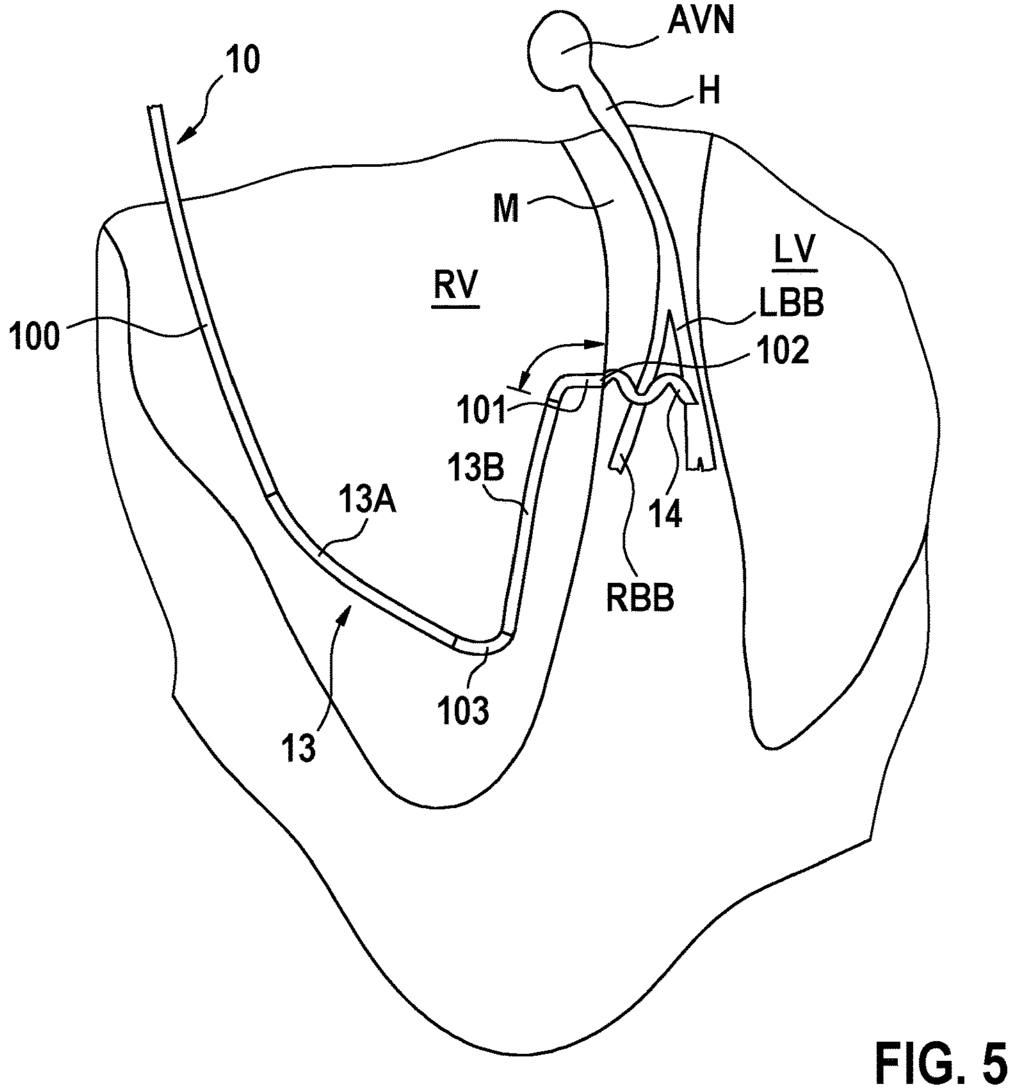
FIG. 5 shows a view of another embodiment of a lead placed in the right ventricle of the heart.

In another embodiment shown in FIG. 5, the electrode device 13 is divided into two electrode sections 13A, 13B which are spatially separated from one another and each are formed as a wound coil. In between the electrode sections 13A, 13B a connection section 103 extends, the connection section 103 having a reduced bending stiffness such that the lead 10 may flexibly bend at the connection section 103 and in particular may assume a rather tight bending radius. Hence, the sections 13A, 13B of the electrode device 13 may be arranged at a sharp angle with respect to one another, which facilitates the arrangement of the electrode device 13 in the region of the vertex of the right ventricle RV, as visible from FIG. 5.

Both in the embodiment of FIG. 2 and in the embodiment of FIG. 5 the electrode device 13 may extend from the right ventricle RV into the right atrium RA.

In either embodiment, the body section 100 may form an inner lumen into which, for example, a locking stylet may be inserted in order to facilitate an explantation of the lead 10. By means of the locking stylet a pulling force may be exerted on the distal lead section 101, the locking stylet preventing an axial deformation of the electrode device 13.

Electrical conductors may be embedded within the body section 100 and the distal lead section 101 in order to electrically connect the electrode device 13 of the electrode device 14 to the connector 16 for connection to the generator 12.

The idea of the present invention is not limited to the embodiments described above, but may be implemented in an entirely different manner.

One or multiple leads may be used on a generator. The leads herein may provide for a pacing and/or sensing of electrical signals at different locations within the heart. One or multiple leads, in addition to a pacing and/or sensing electrode, may comprise a defibrillation (shock) electrode such that, using a single lead, a pacing function as well as a defibrillation function may be provided.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantable medical device
10 Lead
100 Body section
101 Distal lead section
102 Distal end
103 Connection section
11 Lead
12 Generator
13 Electrode device
13A, 13B Electrode section
14 Electrode device
140 Screw body
141 Conducting core
142 Insulation layer
143 Contact section (free end)
15 Reservoir
16 Connector
160 Contact elements
AVN Atrioventricular node
D1, D2 Diameter
H HIS bundle
L Longitudinal axis
L1, L2, L3 Length
LA Left atrium
LBB Left bundle branch
LV Left ventricle
M Intra-cardiac tissue (myocardium)
RA Right atrium
RBB Right bundle branch
RV Right ventricle
SAN Sinoatrial node
V Superior vena

What is claimed is:

1. A lead for an implantable stimulation device for cardiac stimulation of a patient, the lead generally extending along a longitudinal axis and comprising:

a body section including an electrically conductive core,
a distal lead section extending from the body section along the longitudinal axis and forming a distal end, wherein the electrically conductive core is only exposed towards an outside of the body section at the distal end,
a first electrode device arranged on the distal lead section for at least one of transmitting an electrical pacing signal and sensing an electrical sense signal, wherein:
the first electrode device has a shape of a screw and is configured to engage with intra-cardiac tissue,
the first electrode device is configured to pierce into intra-cardiac tissue for fixing the lead at the distal end to intra-cardiac tissue,
the first electrode device extends from the distal end by a length, as measured along the longitudinal axis, and is configured to reach into a left bundle branch of the cardiac conduction system for injecting a pacing signal into the left bundle branch or receiving sense signals from the left bundle branch, and
a second electrode device arranged on the body section for emitting an electrical defibrillation signal,
wherein the entire distal lead section has a first isodiametric cross-sectional shape defined by a first diameter and the entire body section has a second isodiametric cross-sectional shape defined by a second diameter, wherein the first diameter is smaller than the second diameter which results in reduced bending stiffness of the distal lead section with respect to the body section.

2. The lead according to claim 1, wherein the distal lead section comprises a length, measured between the distal end and the body section, equal to or larger than 10 mm.

3. The lead according to claim 1, wherein the distal lead section comprises at least one drug eluting reservoir.

4. The lead according to claim 1, wherein the second electrode device comprises a helical coil-shape.

5. The lead according to claim 1, wherein the second electrode device comprises at least a first electrode section and a second electrode section, wherein the lead comprises a connection section extending in between the first electrode section and the second electrode section.

6. The lead according to claim 5, wherein the connection section in at least one portion comprises a reduced bending stiffness with respect to a portion of said body section carrying the first electrode section and/or to a portion of said body section carrying the second electrode section.

7. A method for operating an implantable stimulation device for cardiac stimulation of a patient, comprising:

providing a lead generally extending along a longitudinal axis, the lead comprising a body section including an electrically conductive core and a distal lead section extending from the body section along the longitudinal axis and forming a distal end, wherein the electrically conductive core is only exposed towards an outside of the body section at the distal end, the lead further comprising a first electrode device having a shape of a screw, the first electrode device configured for at least one of transmitting an electrical pacing signal and sensing an electrical sense signal and a second electrode device arranged on the body section for emitting an electrical defibrillation signal, the first electrode device is configured to pierce into intra-cardiac tissue for fixing the lead at the distal end to intra-cardiac tissue, the first electrode device extending from the distal end by a length, as measured along the longitudinal axis, and is configured to reach into a left bundle branch of the cardiac conduction system for injecting a pacing signal into the left bundle branch or receiving sense signals from the left bundle branch, wherein the entire distal lead section has a first isodiametric cross-sectional shape defined by a first diameter and the entire body section has a second isodiametric cross-sectional shape defined by a second diameter, wherein the first diameter is smaller than the second diameter which results in reduced bending stiffness of the distal lead section with respect to the body section, using the first electrode device, which is engaged with intra-cardiac tissue to reach into a left bundle branch of the cardiac conduction system, to at least one of inject pacing signals into or receive sense signals from the left bundle branch.

8. The lead according to claim 1, wherein the distal lead section comprises a length, measured between the distal end and the body section, equal to or larger than 50 mm.

* * * * *